(12) United States Patent
Wong et al.

(10) Patent No.: US 11,957,620 B2
(45) Date of Patent: Apr. 16, 2024

(54) LEARNING AUTO PHACO PHACOEMULSIFICATION MODE FOR OPHTHALMIC SURGERY

(71) Applicant: JOHNSON & JOHNSON SURGICAL VISION, INC., Irvine, CA (US)

(72) Inventors: Wayne Wong, Irvine, CA (US); Kirk Todd, Yorba Linda, CA (US); Johan Ekvall, Laguna Beach, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 836 days.

(21) Appl. No.: 16/460,978

(22) Filed: Jul. 2, 2019

(65) Prior Publication Data

US 2020/0107958 A1    Apr. 9, 2020

Related U.S. Application Data

(63) Continuation-in-part of application No. 16/151,261, filed on Oct. 3, 2018, now Pat. No. 11,141,313.

(51) Int. Cl.
*A61F 9/007* (2006.01)
*A61M 1/00* (2006.01)
(Continued)

(52) U.S. Cl.
CPC ............ *A61F 9/00745* (2013.01); *A61M 1/77* (2021.05); *A61B 2017/00199* (2013.01);
(Continued)

(58) Field of Classification Search
CPC ... A61F 9/00745; A61F 9/00781; A61M 1/84; A61M 1/0003; A61M 1/0058;
(Continued)

(56) References Cited

U.S. PATENT DOCUMENTS

| 5,160,317 A | 11/1992 | Costin |
| 5,279,547 A | 1/1994 | Costin |

(Continued)

FOREIGN PATENT DOCUMENTS

| DE | 3234621 A1 | 3/1984 |
| EP | 0741554 A1 | 11/1996 |

(Continued)

OTHER PUBLICATIONS

International Search Report for Application No. PCT/IB2020/055973, dated Sep. 10, 2020, 2 pages.

(Continued)

*Primary Examiner* — Ariana Zimbouski
*Assistant Examiner* — John A Doubrava
(74) *Attorney, Agent, or Firm* — Johnson & Johnson Surgical Vision, Inc.

(57) ABSTRACT

A system for learning actual phacoemulsification energy setpoints at the time of occlusion breaks during ophthalmic surgery. Phacoemulsification energy setpoints may be recorded over different periods of time, such as during current cases and over a lifetime of cases. The recorded data would then be used to determine future phacoemulsification energy setting amounts.

15 Claims, 4 Drawing Sheets

(51) Int. Cl.
    *A61B 17/00*     (2006.01)
    *A61B 34/00*     (2016.01)

(52) U.S. Cl.
    CPC ......... *A61B 34/25* (2016.02); *A61B 2217/005* (2013.01); *A61F 9/00781* (2013.01); *A61M 1/60* (2021.05); *A61M 2210/0612* (2013.01)

(58) Field of Classification Search
    CPC ........... A61M 2210/0612; A61B 34/25; A61B 2017/00199; A61B 2217/005
    See application file for complete search history.

(56) References Cited

U.S. PATENT DOCUMENTS

| | | | |
|---|---|---|---|
| 5,733,256 | A | 3/1998 | Costin |
| 5,836,990 | A | 11/1998 | Li |
| 6,690,280 | B2 | 2/2004 | Citrenbaum et al. |
| 8,246,580 | B2 | 8/2012 | Hopkins et al. |
| 8,414,605 | B2 | 4/2013 | Gordon et al. |
| 8,523,812 | B2 | 9/2013 | Boukhny et al. |
| 8,597,228 | B2 | 12/2013 | Pyles et al. |
| 9,144,517 | B2 | 9/2015 | Kuebler et al. |
| 9,282,989 | B2 | 3/2016 | Boukhny et al. |
| 9,545,335 | B2 | 1/2017 | Boukhny et al. |
| 9,707,127 | B2 | 7/2017 | Kadziauskas |
| 9,999,710 | B2 | 6/2018 | Ross et al. |
| 10,045,882 | B2 | 8/2018 | Balicki et al. |
| 10,070,988 | B2 | 9/2018 | McDonell et al. |
| 10,219,940 | B2 | 3/2019 | Raney et al. |
| 10,368,760 | B2 | 8/2019 | Hauck |
| 10,453,571 | B2 | 10/2019 | Teodorescu |
| 10,463,780 | B2 | 11/2019 | Mallough et al. |
| 10,596,033 | B2 | 3/2020 | Urich et al. |
| 10,940,039 | B2 | 3/2021 | Banko |
| 2004/0092800 | A1 | 5/2004 | Mackool |
| 2004/0193182 | A1 | 9/2004 | Yaguchi et al. |
| 2005/0209560 | A1 | 9/2005 | Boukhny et al. |
| 2005/0261628 | A1 | 11/2005 | Boukhny et al. |
| 2006/0079788 | A1 | 4/2006 | Anderson et al. |
| 2006/0100570 | A1 | 5/2006 | Urich et al. |
| 2006/0129140 | A1 | 6/2006 | Todd et al. |
| 2007/0073309 | A1 | 3/2007 | Kadziauskas et al. |
| 2007/0161972 | A1 | 7/2007 | Felberg et al. |
| 2008/0064935 | A1* | 3/2008 | Wong ................ G16H 40/63 600/300 |
| 2009/0118663 | A1 | 5/2009 | Rockley et al. |
| 2009/0182266 | A1 | 7/2009 | Gordon et al. |
| 2010/0069825 | A1 | 3/2010 | Raney |
| 2010/0118266 | A1* | 5/2010 | Nixon ................ A61B 3/1173 351/246 |
| 2010/0287127 | A1 | 11/2010 | Claus et al. |
| 2011/0015563 | A1* | 1/2011 | Boukhny ....... A61B 17/320068 604/22 |
| 2011/0313280 | A1 | 12/2011 | Govari et al. |
| 2012/0232466 | A1 | 9/2012 | Kuebler et al. |
| 2014/0018724 | A1 | 1/2014 | Staggs |
| 2014/0114296 | A1 | 4/2014 | Woodley et al. |
| 2014/0316254 | A1 | 10/2014 | Eversull et al. |
| 2014/0323953 | A1 | 10/2014 | Sorensen et al. |
| 2015/0073816 | A1* | 3/2015 | Ha .................. G16H 40/63 705/2 |
| 2015/0216726 | A1 | 8/2015 | Kadziauskas et al. |
| 2016/0175543 | A1 | 6/2016 | Frankhouser et al. |
| 2018/0028359 | A1 | 2/2018 | Gordon et al. |
| 2018/0092555 | A1 | 4/2018 | Script |
| 2018/0207330 | A1 | 7/2018 | Ovchinnikov et al. |
| 2018/0318131 | A1 | 11/2018 | Boukhny et al. |
| 2020/0309760 | A1 | 10/2020 | Durant |
| 2021/0196515 | A1 | 7/2021 | Urich |
| 2021/0361481 | A1 | 11/2021 | Gliner et al. |
| 2022/0008251 | A1 | 1/2022 | Govari et al. |
| 2022/0313489 | A1 | 10/2022 | Hajishah et al. |
| 2023/0043082 | A1 | 2/2023 | Govari et al. |
| 2023/0285189 | A1 | 9/2023 | Govari |
| 2023/0320897 | A1 | 10/2023 | Hajishah et al. |

FOREIGN PATENT DOCUMENTS

| | | |
|---|---|---|
| EP | 0956840 A2 | 11/1999 |
| EP | 1935383 A1 | 6/2008 |
| EP | 1743309 B1 | 10/2011 |
| EP | 3448235 A2 | 3/2019 |
| JP | 4126304 B2 | 7/2008 |
| WO | 9211814 A1 | 7/1992 |
| WO | 2008016870 A2 | 2/2008 |
| WO | 2010014937 A1 | 2/2010 |
| WO | 2016122790 A1 | 8/2016 |
| WO | 2019069201 A1 | 4/2019 |
| WO | 2021119616 A1 | 6/2021 |

OTHER PUBLICATIONS

Co-pending U.S. Appl. No. 17/954,613, inventors Govari; Assaf et al., filed Sep. 28, 2022.

Co-pending U.S. Appl. No. 17/971,936, inventor Govari; Assaf, filed Oct. 24, 2022.

Co-pending U.S. Appl. No. 18/203,673, inventors Vadim; Gliner et al., filed May 31, 2023.

U.S. Appl. No. 16/727,100, titled "Phacoemulsification Apparatus," filed Dec. 26, 2019.

U.S. Appl. No. 17/357,587, titled, "Accurate Irrigation Rate Measurment System and Method," filed Jun. 24, 2021.

\* cited by examiner

LEARNING AUTO PHACO PHACOEMULSIFICATION MODE FOR OPHTHALMIC SURGERY

CROSS-REFERENCE TO RELATED APPLICATIONS

The present application claims priority to and is a continuation-in-part application to U.S. application Ser. No. 16/151,261, filed on Oct. 3, 2018, which is herein incorporated by reference in its entirety.

BACKGROUND

Field of Invention

The present disclosure relates to a learning auto phacoemulsification mode for ophthalmic surgery and, more specifically, the learning of actual phaco energy setpoints over a period of time which then is recorded during an occlusion break.

Description of Related Art

During ophthalmic surgery, an ophthalmic surgical apparatus is used to perform surgical procedures in a patient's eye. An ophthalmic surgical apparatus typically includes a handheld medical implement or tool, such as a handpiece with a tip and/or sleeve, and operating controls for regulating settings or functions of the apparatus and tool. Operation of the tool requires control of various operating settings or functions based on the type of tool used. Such apparatuses typically include a control module, power supply, an irrigation source, one or more aspiration pumps, as well as associated electronic hardware and software for operating a multifunction handheld surgical tool. The handpiece may include a needle or tip which is ultrasonically driven once placed with the incision to, for example, emulsify the lens of the eye. In various surgical procedures, these components work together to, for example, emulsify eye tissue, irrigate the eye with a saline solution, and aspirate the emulsified lens from the eye.

Intraocular pressure (IOP) is the fluid pressure inside the anterior chamber of the eye. In a normal eye, intraocular pressure may vary depending on the time of day, activities of the patient, fluid intake, medications, etc. Intraocular pressure may be measured as static (a specific value) or dynamic (a range of values). As can be appreciated, the static IOP and dynamic IOP of a patient's eye can fluctuate greatly during an ophthalmic surgery procedure. It is well known that the IOP in an anterior chamber of the eye is required to be controlled and maintained during such surgical procedures to avoid damage to the patient's eye. For the correct function of the eye and its structure (e.g. shape) and to preserve sharp and undamaged vision, it is very important to keep the IOP in normal, physiological values.

An exemplary type of ophthalmic surgery is phacoemulsification. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes one or more irrigation ports proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the patient's eye, to establish positive pressure by gravity, and/or with external pressure source) is irrigated into the eye via the irrigation line and the irrigation port(s). This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material is aspirated or removed from the eye by the aspiration pump and line via the aspiration port.

Similarly, cataract surgery is a complex procedure performed by highly skilled surgeons using extremely complex and expensive equipment. The surgeon undergoes years of training to perfect their technique while using only a fraction of the system's capabilities and features. For example, cataract tissue, which may be denser, may be removed by aspiration. When the material has been emulsified or softened to the point where aspiration is sufficient to remove the material an occlusion break occurs. It is well-known that excessive energy application after an occlusion break occurs, known as a post-occlusion surge, could potentially damage the tissue. In practice, the surgeon may anticipate this occurrence and discontinue ultrasonic power to prevent any damage to the eye. If the occlusion break occurs faster than the surgeon can discontinue power, the surgeon may apply more power than needed. Studies have shown that the human reaction time is approximately 350 milliseconds (ms). That means the patient may be subjected to an additional 350 ms or more of ultrasonic energy every occlusion break.

For example, during segment removal, the surgeon may confront a multitude of decisions as he/she attempts to balance the inflow and outflow of fluid in the eye while trying to control the movement of material with the handpiece and deciding when to apply ultrasonic power. Additionally, lens material may create a blockage at the tip preventing fluid from being evacuated. This blockage can result in post-occlusion surge and lead to eye trauma. When faced with a potential post-occlusion surge situation, the surgeon has to decide whether to preempt the surge by clearing the occlusion by applying power to knock the piece off the tip and having to reacquire the piece or discontinue the procedure by gradually (or quickly) releasing the foot pedal to change the pump speed and/or vacuum. Depending on the density of the material, length of occlusion, maximum aspiration rate, maximum vacuum and a wide variety of other factors, the occlusion may clear before the surgeon can take action. A disadvantage in releasing the footpedal is the fact that cataract lens material in the aspirating phacoemulsification handpiece may flow back into the eye chamber leading to a longer, less efficient cataract extraction.

Techniques to overcome post-occlusion surge have been developed that include smaller or specialized tips that allow fluid to enter through a secondary port to allow continuous fluid flow. Alternatively, other techniques include modifying predefined vacuum or aspiration settings, adjusting vacuum manually during the procedure or automatically "on-the-fly", and releasing the foot pedal to discontinue aspiration. These techniques have had varying levels of success.

Other techniques include steps to ramp from a user-defined baseline phaco energy setting on occlusion onset until the occlusion has cleared. The user-defined baseline setting, if too low, may cause extra phaco time due to the time required to ramp to an occlusion break power. On the other hand, if the user-defined baseline is too high, an excess of phaco energy can, and will, be imparted to the patient's eye.

SUMMARY

The present invention provides a system for recording, over a period of time, energy setpoints at the time of occlusion breaks. The recorded values, or Occlusion Break Values, provide data points to be inputted to assist in deriving and determining what is considered to be a phaco energy setting amount for phacoemulsification surgery when taken in combination with a myriad of different parameters, such as lifetime recorded values, surgeon-specific data inputs, and cataract grades, or the like. The baseline phaco energy setting amount is therefore considered to be a learned value based on historical data gathered from prior as well as current phacoemulsification surgical procedures.

An auto phaco phacoemulsification system for learning phaco energy setpoints during phacoemulsification surgery is disclosed, the system comprising a surgical console having at least one system bus communicatively connected to at least one computing processor capable of accessing at least one computing memory associated with the at least one computing processor, wherein the surgical console is configured to determine an energy setpoint based on one or more values recorded in response to one or more occlusion breaks; and at least one vacuum source associated with the surgical console for providing a vacuum pressure and at least one energy source associated with the surgical console for providing ultrasonic energy based on the determined energy setpoint.

BRIEF DESCRIPTION OF THE DRAWINGS

The organization and manner of the structure and function of the disclosure, together with the further objects and advantages thereof, may be understood by reference to the following description taken in connection with the accompanying drawings, and in which.

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

Figure 1:
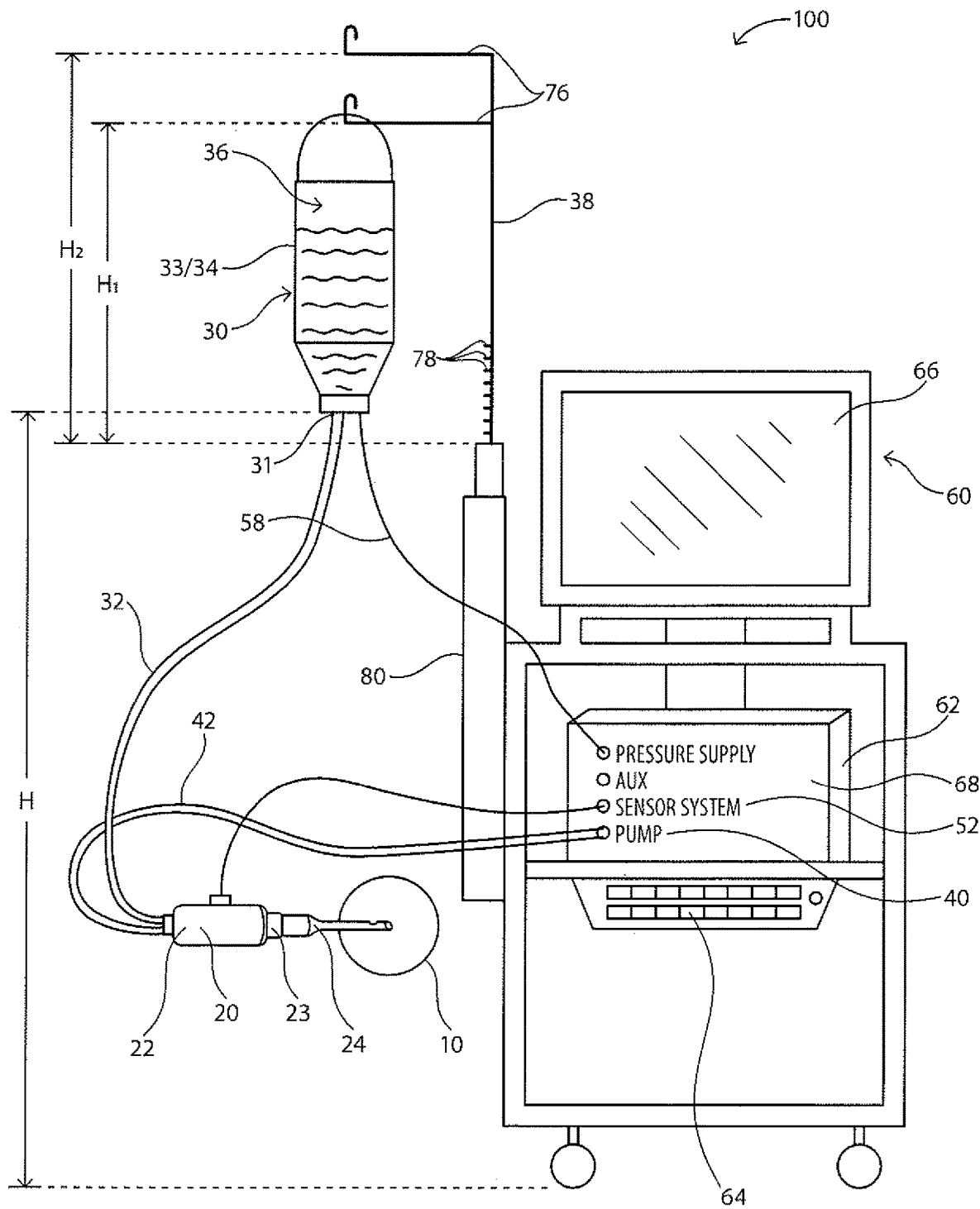
FIG. 1 illustrates a diagram of an exemplary phacoemulsification/diathermy/vitrectomy system in accordance with the present disclosure, the system including a control module to control various features of the system.
Figure 2:
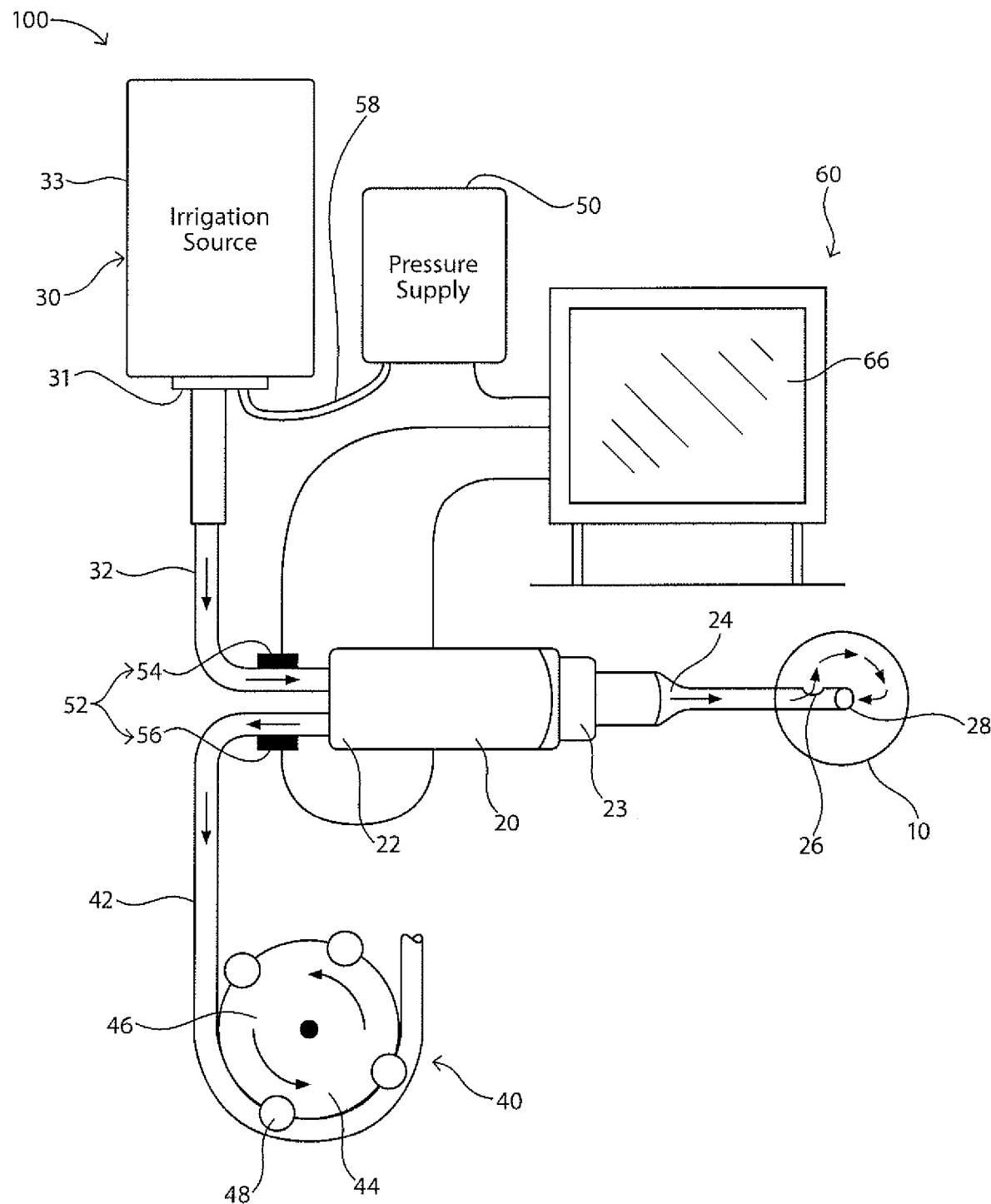
FIG. 2 illustrates an alternative phacoemulsification/diathermy/vitrectomy system and illustrated connected to various components of the system in order to determine characteristics or features of the components.

FIGS. 1 and 2 illustrate an exemplary phacoemulsification/diathermy/vitrectomy system 100. As illustrated, the system 100 includes, for example, a handpiece or wand 20, an irrigation source 30, an aspiration source 40, an optional pressure supply 50, and a control module 60. In illustrative embodiments, fluid is controllably directed through the system 100 in order to irrigate a patient's eye, illustrated representatively at 10, during an ocular surgical procedure. Various embodiments of the handpiece 20, irrigation source 30, aspiration source 40, optional pressure supply 50 and control module 60 are well-known in the art and are embodied in this disclosure.

As illustrated in FIGS. 1 and 2, the irrigation source 30 is configured to supply a predetermined amount of fluid to the handpiece 20 for use during a surgical operation. Such fluid is supplied to, for example, stabilize or maintain a certain Intraocular Pressure (IOP) in the anterior chamber of the eye during surgery, as well as provide means for fluidly transporting any particles (e.g. lens particulates that are created during emulsification) out of the eye. Various aspects (e.g. the flow rate, pressure) of fluid flow into and out of the anterior chamber of the eye will typically affect the operations of the surgical procedure.

In illustrative embodiments, fluid may flow from the irrigation source 30 to the handpiece 20 via an irrigation line 32. The irrigation source 30 may be any type of irrigation source 30 that can create and control a constant fluid flow. In illustrative embodiments, the irrigation source is elevated to a predetermined height via an extension arm 38. In illustrative embodiments, the irrigation source 30 may be configured to be an elevated drip bag 33/34 or bottle that supplies a steady state of fluid 36 to the irrigation line 32. The pressure supply 50/58 may be coupled to the irrigation source 30 in order to maintain a constant pressure in the irrigation source 30 as fluid exits the irrigation source 30, as is known in the industry. Other embodiments of a uniform irrigation source are well-known in the art.

During the surgical procedure, it is typically necessary to remove or aspirate fluid and other material from the eye. Accordingly, fluid may be aspirated from the patient's eye, illustrated representatively at 10, via the handpiece 20 to flow through an aspiration line 42 to the aspiration source 40. The aspiration source 40 may be any type of aspiration source 40 that aspirates fluid and material from the eye. In illustrative embodiments, the aspiration source 40 may be configured to be a flow-based pump 44 (such as a peristaltic pump) or a vacuum-based pump (such as a Venturi pump) that are well-known in the art. The aspiration source 40 may create a vacuum system to pump fluid and/or material out of the eye via the aspiration line 42. A sensor system 52 may be present to measure the pressure, flow and/or vacuum that the aspiration source 40 creates. The sensor may be located anywhere in the handpiece and/or system. Other embodiments of an aspiration source are well-known in the art.

The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The pressure in the aspiration line may be measured by the system, e.g. by the sensor system 52. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well-known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing a crystalline lens also typically include irrigating the eye and aspirating lens parts and other liquids. Additionally, other procedures may include irrigating the eye and aspirating the irrigating fluid within concomitant destruction, alternation or removal of the lens.

The aspiration source 40 is configured to aspirate or remove fluid and other materials from the eye in a steady, uniform flow rate. Various means for steady, uniform aspiration are well-known in the art. In illustrative embodiments, the aspiration source 40 may be a Venturi pump, a peristaltic pump, or a combined Venturi and peristaltic pump. In illustrative embodiments, and as shown in FIG. 2, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well-known in the art. When the aspiration source 40 includes a combined Venturi and peristaltic pump, the aspiration source 40 may be controlled to automatically switch between the two types of pumps or user controlled to switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64, and a display or screen 66, as illustrated in FIGS. 1 and 2. The microprocessor computer 62 may be operably connected to and control the various other elements of the system, while the keyboard 64 and display 66 permit a user to interact with and control the system components as well. In an embodiment a virtual keyboard on display 66 may be used instead of keyboard 64. A system bus 68 may be further provided to enable the various elements to be operable in communication with each other. The control module 60 may be powered by an energy source. One skilled in the art would appreciate that the energy source may be a power source— such as a 110 v plug—or conventional commercial power sources.

The screen 66 may display various measurements, criteria or settings of the system 100—such as the type of procedure, the phase of the procedure and duration of the phase, various parameters such as vacuum, flow rate, power, and values that may be input by the user, such as bottle height, sleeve size, tube length (irrigation and aspiration), tip size, vacuum rate, etc. The screen 66 may be in the form of a graphical user interface (GUI) associated with the control module 60 and utilizing a touchscreen interface, for example. The GUI may allow a user to monitor the characteristics of the system 100 or select settings or criteria for various components of the system. For instance, the GUI may permit a user to select or alter the maximum pressure being supplied by the pressure supply 50 to the irrigation source 30 via line 58. The user may further control the operation of the phase of the procedure, the units of measurement used by the system 100, or the height of the irrigation source 30, as discussed below. The GUI may further allow for the calibration and priming of the pressure in the irrigation source 30.

In illustrative embodiments, the system 100 may include a sensor system 52 configured in a variety of ways or located in various locations. For example, the sensor system 52 may include at least a first sensor or strain gauge 54 located along the irrigation line 32 and a second sensor or strain gauge 56 located along the aspiration line 42, as illustrated in FIG. 2. Other locations for the sensors 54 and 56 are envisioned anywhere in the system 100, e.g. on the handpiece 20, and may be configured to determine a variety of variables that may be used to determine pressure measurements in the aspiration line, as discussed below. This information may be relayed from the sensor system 52 to the control module 60 to be used in the determination of the presence of an occlusion break. The sensor system 52 may also include sensors to detect other aspects of the components used in the system, e.g. type of pump used, type of sleeve used, gauge of needle tip (size), etc.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

The present invention may learn from data derived during a phacoemulsification surgical procedure as part of an Auto Phaco phacoemulsification system. This learned data may then be utilized to calculate what is called a baseline phaco energy setting amount. In an exemplary embodiment of the present invention, data may be derived from an actual phaco energy setpoint recorded at the time of an Auto Phaco occlusion break. An immediate occlusion onset/break may be recorded as an excess of phaco energy condition and in turn cause the learned value to decrease. The recorded values, also called Occlusion Break Values (OBV) may be recorded in a memory or suitable database management system. Other data storage techniques or devices may be used to provide adequate security to ensure privacy of patient data. The stored OBV may be kept for a current case, such as during a current phacoemulsification surgical procedure, or over a lifetime of cases. For example, lifetime recorded values may be learned over many cases, such as more than five cases, for example, and may be contained in an individual surgeon's saved data file. Even further, recorded values may be saved independently and may be associated with a cataract grade. Any suitable cataract grading formula or method may be used, such as the Lens Opacities Classification System III. Lifetime learned values may also contain a deviation value. The deviation value may be used to track the variability of a surgeon's decision-making judgements with regard to a certain cataract grade. This Lifetime variability value may then be used to determine a phaco energy setting amount to subtract from a learned Lifetime OBV for an Auto Phaco ramp starting point for a first Auto Phaco occlusion occurrence during a current case. Subsequent Auto Phaco ramp setpoints during the same case may then use the case-learned OBV minus the case variability value.

Figure 3:
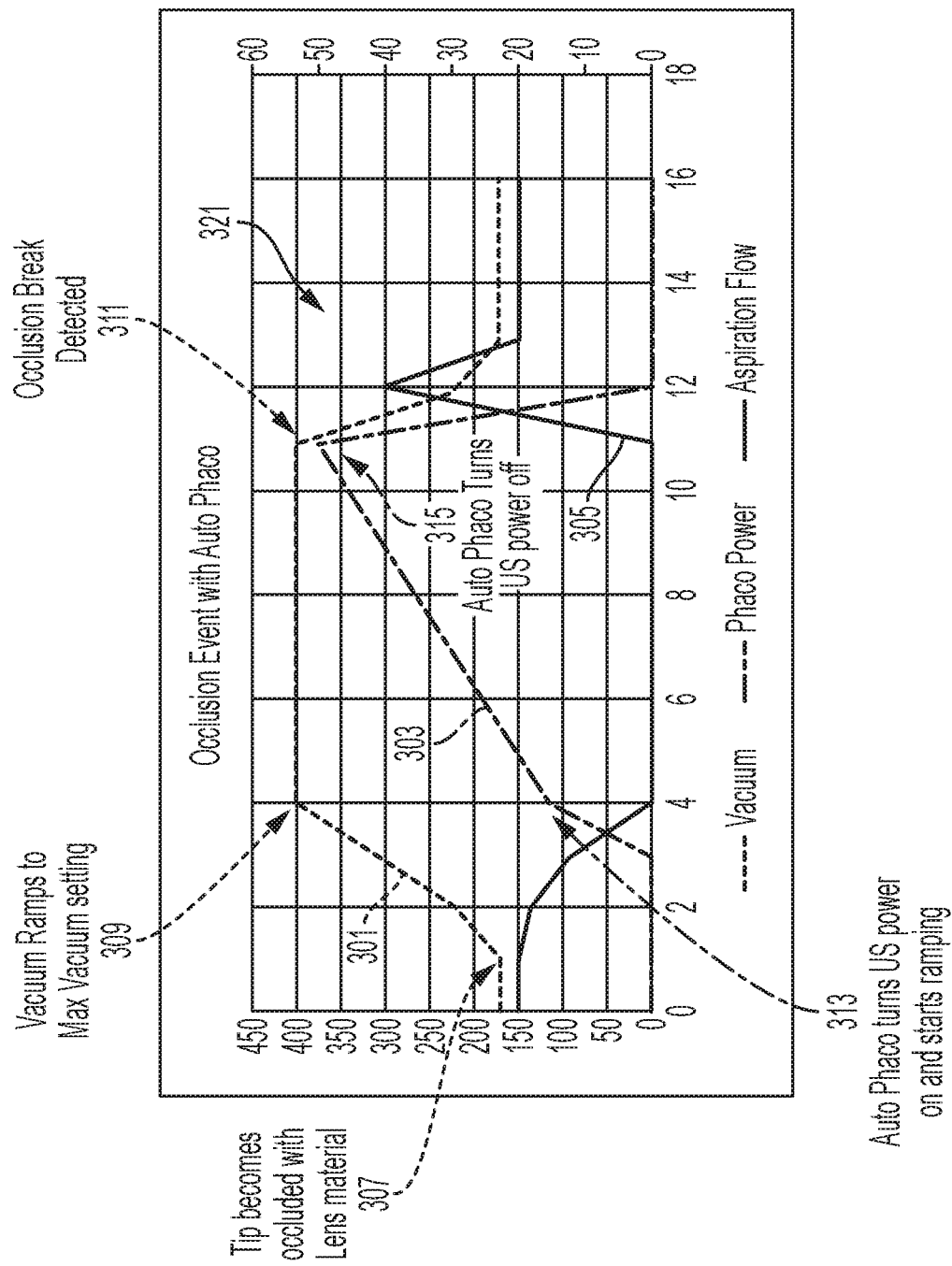
FIG. 3 illustrates a graphical representation of an embodiment of Auto Phaco.

In an embodiment, and by way of an example, FIG. 3 provides a graphical explanation of Auto Phaco. Ultrasound (US) phaco time and accumulated power have been shown to have a detrimental effect on endothelial cell densities. Surgeons routinely track the US time and accumulated power imparted to each patient's eye. The Auto Phaco phacoemulsification system minimizes this power by only turning on power when there is an occlusion event 321. In FIG. 3, occlusion event 321 is shown and the relationship between the vacuum level changes (line 301), phaco power level changes (line 303), and aspiration flow rate changes (line 305) are shown. For vacuum, the time point when the tip becomes occluded with lens material 307, the vacuum ramp to the maximum vacuum setting 309, and the occlusion break detected 311 are illustrated. For phaco power, the point at which Auto Phaco turns the US power on and starts to ramp up 313 and the point at which Auto Phaco turns off the US power because of the occlusion break detected 315 are illustrated. Finally, line 305 shows the relationship of the aspiration flow with respect to the other two parameters.

Figure 4:
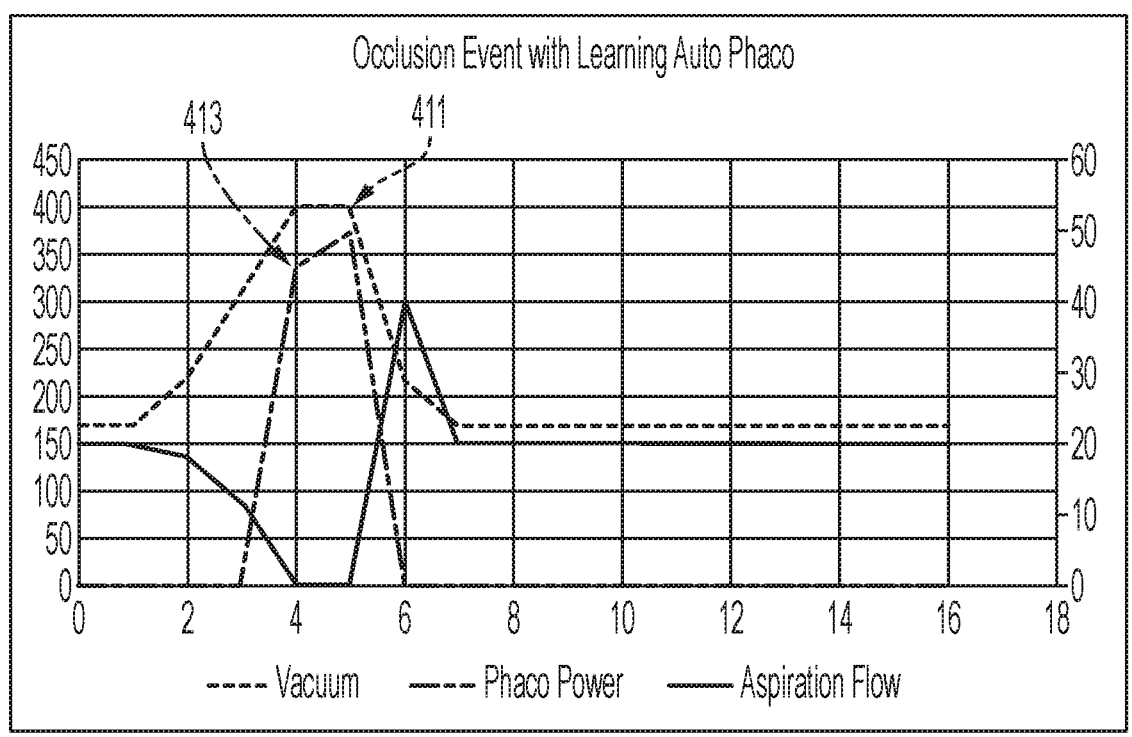
FIG. 4 illustrates a graphical representation of an embodiment of Auto Phaco.

In an embodiment, the Auto Phaco may be able to set the Auto Phaco start point as close to the occlusion break setting as possible. A means of doing this would be for the phacoemulsification system to keep track of and learn the occlusion break setting. In addition, the cataract hardness (cataract grade) may affect the occlusion breakpoint setting. The Auto Phaco phacoemulsification system may learn the mean occlusion break setting on a per surgeon, and/or per selected cataract grade basis. The surgeon's capability of judging the cataract grade before surgery may vary between surgeons. In an embodiment, the Auto Phaco phacoemulsification system keeps track of the stored mean deviation between the stored value and the value where occlusion break happens on a per surgeon and/or per cataract grade basis and use this value to adjust the ramp start value to accommodate for the variation. The better the surgeon can judge a cataract hardness the less US power would be needed. In FIG. 4, the ramp start setpoint 413 is 5% below the occlusion break value 411 than that shown on FIG. 3. The 5% value is based on an example of a particular surgeon's deviation value.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

What is claimed is:

1. An auto phaco phacoemulsification system for learning phaco energy setpoints during phacoemulsification surgery, the system comprising:
 a surgical console having at least one system bus communicatively connected to at least one computing processor capable of accessing at least one computing memory associated with the at least one computing processor, wherein the surgical console is configured to determine a phaco energy baseline setpoint to ramp phaco energy on occurrence of an occlusion at a tip of a phaco instrument, the phaco energy baseline setpoint based on one or more values recorded in response to one or more prior occlusion breaks, wherein the phaco energy baseline setpoint is a phaco energy setting amount; and
 at least one vacuum source associated with the surgical console for providing a vacuum pressure and at least one energy source associated with the surgical console for providing ultrasonic energy based on the determined phaco energy baseline setpoint.

2. The system of claim 1, wherein each of the occlusion breaks is recorded as a lens emulsifying condition.

3. The system of claim 1, wherein the one or more values are based on occlusion breaks occurring during a single surgical procedure.

4. The system of claim 1, wherein the one or more values are based on occlusion breaks occurring over a plurality of surgical procedures.

5. The system of claim 1, wherein the one or more values are based on estimated values for occlusion breaks occurring during a plurality of surgical procedures.

6. The system of claim 1, wherein the phaco energy baseline setpoint decreases in response to an excess energy condition.

7. The system of claim 1, wherein a deviation value is determined based on the one or more values.

8. The system of claim 7, wherein the phaco energy baseline setpoint is determined by subtracting the deviation value from a mean average of historical occlusion break values.

9. The system of claim 8, wherein the deviation value is based at least in part on surgeon decision-making parameters and a cataract grade.

10. The system of claim 9, wherein the cataract grade is based on the Lens Opacities Classification System II grading system.

11. A system having at least one processor coupled to a memory, the system configured to record, over a period of time, energy setpoints at the time of one or more phacoemulsification occlusion breaks and subsequently set at least one phaco energy baseline setpoint to ramp phaco energy on occurrence of an occlusion at a tip of a phaco instrument for phacoemulsification surgery based at least in part on the recorded energy setpoints, wherein each of the energy setpoints are a phaco energy setting amount.

12. An auto phaco phacoemulsification system having at least one processor coupled to a memory, the system configured to set an auto phaco ramp starting point by subtracting from a lifetime occlusion break value a lifetime variability value.

13. The system of claim 12, wherein the lifetime variability value is based on a deviation value.

14. The system of claim 13, wherein the deviation value is based at least in part on a timing of a surgeon's decision-making and cataract grade during an occlusion break value recording event.

15. The system of claim 14, wherein the lifetime occlusion break value is based on historical data gathered in response to occlusion breaks occurring during one or more prior phacoemulsification surgical procedures.

* * * * *